United States Patent [19]

Doi et al.

[11] Patent Number: 4,839,807
[45] Date of Patent: Jun. 13, 1989

[54] METHOD AND SYSTEM FOR AUTOMATED CLASSIFICATION OF DISTINCTION BETWEEN NORMAL LUNGS AND ABNORMAL LUNGS WITH INTERSTITIAL DISEASE IN DIGITAL CHEST RADIOGRAPHS

[75] Inventors: Kunio Doi, Willowbrook; Shigehiko Katsuragawa, Clarendon Hills, both of Ill.

[73] Assignee: University of Chicago, Chicago, Ill.

[21] Appl. No.: 126,847

[22] Filed: Nov. 27, 1987

Related U.S. Application Data

[63] Continuation-in-part of Ser. No. 81,143, Aug. 3, 1987.

[51] Int. Cl.$^4$ ............................................. G06F 15/42
[52] U.S. Cl. ......................... 364/413.13; 364/413.01; 382/6; 378/901
[58] Field of Search ...................... 364/414; 378/401; 382/4, 6

[56] References Cited

U.S. PATENT DOCUMENTS

| | | | |
|---|---|---|---|
| 3,980,885 | 9/1976 | Steward | 250/307 |
| 4,411,270 | 10/1983 | Damadian | 128/653 |
| 4,437,161 | 3/1984 | Anderson | 364/414 |
| 4,545,068 | 3/1985 | Tabata | 382/41 |
| 4,630,202 | 12/1986 | Mori | 378/901 |
| 4,663,773 | 5/1987 | Haendle | 378/99 |
| 4,682,291 | 7/1987 | Reuveni | 364/414 |
| 4,707,786 | 11/1987 | Dehner | 364/414 |
| 4,723,553 | 2/1988 | Miwa | 128/660 |
| 4,769,850 | 9/1988 | Itoh | 382/6 |

Primary Examiner—Jerry Smith
Assistant Examiner—Gail O. Hayes
Attorney, Agent, or Firm—Oblon, Fisher, Spivak, McClelland & Maier

[57] ABSTRACT

A method and system for automated classification of distinction between normal lungs and abnormal lungs with interstitial disease, based on the analysis of predetermined physical texture measures and also on a data base for normal lungs of these texture measures. The texture measures selected are the RMS variation, R, and the first moment of power spectrum, M, for lung texture. These two texture measures are normalized by using the data base for normal lungs. A single texture index is determined from the two normalized texture measures by taking into account the distribution (or the data base) of texture measures obtained from abnormal lungs, in order to facilitate the automated classification of normal and abnormal lungs. A threshold texture index is then chosen for initial selection of "abnormal" regions of interest (ROIs), which contain a large texture index above the threshold level. The selected abnormal ROIs are then subjected to three independent tests for a (1) definitely abnormal singular pattern, (2) localized abnormal pattern for two or more abnormal clustered ROIs, and (3) diffuse abnormal pattern for more than four abnormal ROIs distributed through the lung. A chest image containing any one of these abnormal patterns is classified as showing an abnormal lung with interstitial disease.

46 Claims, 13 Drawing Sheets

METHOD AND SYSTEM FOR AUTOMATED CLASSIFICATION OF DISTINCTION BETWEEN NORMAL LUNGS AND ABNORMAL LUNGS WITH INTERSTITIAL DISEASE IN DIGITAL CHEST RADIOGRAPHS

CROSS-REFERENCE TO RELATED APPLICATIONS

This application is a continuation-in-part of pending U.S. patent application Ser. No. 07/081,143 filed Aug. 3, 1987, and is related to commonly owned pending U.S. patent application Ser. No. 068,221 filed June 30, 1987 by Doi et al, entitled "Automated system for the Detection of Abnormal Anatomic Regions in a Digital X-ray Image", and Ser. No. 07/081,001 filed Aug. 3, 1987, the disclosures of which are incorporated by reference herein.

BACKGROUND OF THE INVENTION

1. Field of the Invention:

This invention relates to a method and system for automated classification of distinction between normal lungs and abnormal lungs with interstitial disease in digital chest x-rays.

2. Discussion of Background:

In copending parent application Ser. No. 07/081,143 there is described in detail the prior efforts by researchers in the field of automated techniques in diagnostic radiology. In this parent application there is also disclosed and claimed an automated method for detecting and characterizing interstitial lung diseases based on physical measures of lung texture in digital chest radiographs. As described in Ser. No. 07/081,143, approximately twenty square regions of interest (ROIs) are selected from inter-rib spaces by an automated or manual method, and the non-uniform background trend in each ROI is corrected in order to isolate the overall gross lung anatomy from the underlying fine texture which relates to interstitial disease. After the power spectrum of the lung texture is filtered by the visual system response of the human observer, the rms variation and the first moment of the power spectrum are determined as quantitative texture measures of the magnitude and coarseness (or fineness) of the lung texture, respectively. The present invention builds on that disclosed in Ser. No. 081,143 in that the inventor have determined these texture measures for 100 normal lungs and for 100 abnormal lungs with nodular, reticular, and honeycomb patterns, in order to establish a data base. This data base is then used according to the present invention to establish criteria for automated classification of distinction between normal lungs and abnormal lungs with interstitial disease.

SUMMARY OF THE INVENTION

Accordingly, one object of this invention is to provide a novel method and system which provides improved reliability in automated detection of various lung abnormalities.

A further object of this invention is to provide a new and improved method and system for automated detection of various lung abnormalities, which yield superior results in comparison to diagnoses from trained radiologists.

These and other objects are achieved according to the invention by providing a new and improved method and system for automated classification of distinction between normal lungs and abnormal lungs with interstitial disease, based on the analysis of predetermined physical texture measures and also on the data base of these texture measures. The texture measures selected are the RMS variation, R, and the first moment of power spectrum, M, for lung texture, which are derived as described in Ser. No. 07/081,143. First, the two texture measures (the rms variation, R, and the first moment of power spectrum, M, for lung texture), are normalized by using the data base for normal lungs. Then, a single texture index is determined from the two normalized texture measures by taking into account the distribution (or the data base) of texture measures obtained from abnormal lungs, in order to facilitate the automated classification of normal and abnormal lungs. A threshold texture index is then chosen for initial selection of "abnormal" regions of interest (ROIs) which contain a large texture index above the threshold level. The selected abnormal ROIs are then subjected to three independent tests for a (1) definitely abnormal singular pattern, (2) localized abnormal pattern for two or more abnormal clustered ROIs and (3) diffuse abnormal pattern for more than four abnormal ROIs distributed through the lung. A chest image containing any one of these abnormal patterns is classified as showing an abnormal lung with interstitial disease.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
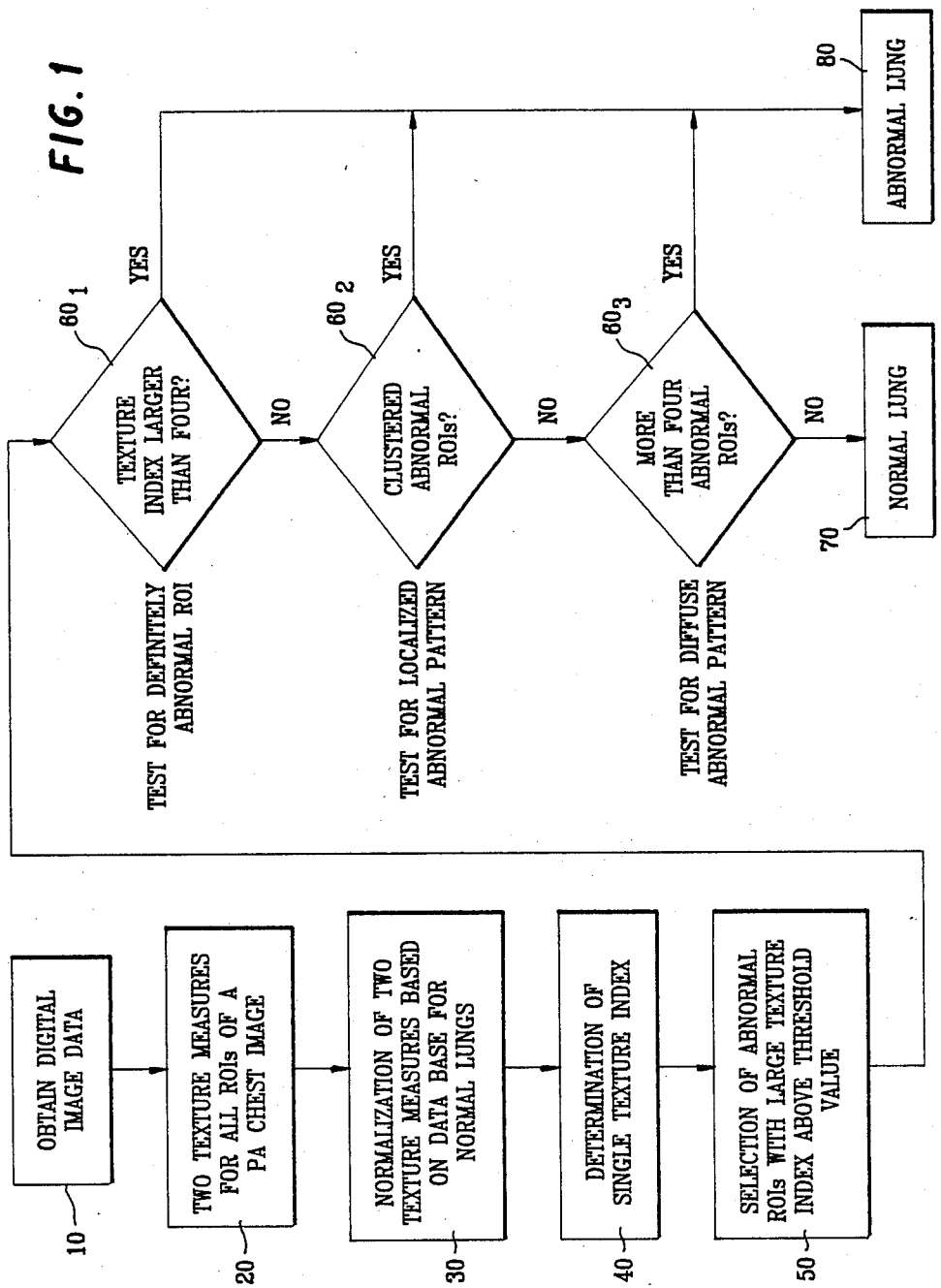
FIG. 1 is a flow chart illustrating the automated classification method for distinction between normal lungs and abnormal lungs with interstitial disease, based on analysis of physical texture measures according to the present invention.

Referring now to the drawings, wherein like reference numerals designate identical or corresponding parts throughout the several views, and more particularly to FIG. 1 thereof, there is shown a flow chart illustrating the method for automated classification of distinction between normal and abnormal lungs according to the present invention. As shown in FIG. 1, in the first step 10 of the invention, digital image data of the subject under diagnosis are obtained. In particular approximately twenty square regions of interest (ROIs) are sampled from inter-rib spaces by an automated or manual method as described in Ser. No. 07/081,143. For each ROI selected in step 20, the rms variation and the first moment of the power spectrum are determined as quantitative texture measures for the magnitude and coarseness (or fineness) of the lung texture, respectively, as also described in Ser. No. 07/081,143. In particular, in obtaining these texture measures, as described in Ser. No. 07/081,143, the non-uniform background trend in each ROI is corrected by means of a two-dimensional (2D) surface fitting technique in order to determine the fluctuating patterns of the underlying lung texture for subsequent computer analysis. The power spectrum of the lung texture is obtained from the 2D Fourier transform and is filtered by the visual system response of the human observer. Finally, the root-mean-square (rms) variation, R, and the first moment of the power spectrum, M, are determined as the noted quantitative texture measures for the magnitude and coarseness (or fineness), respectively, of the lung texture.

In more detail, the 2D Fourier transformed data are defined by $T(u,v)$, where u and v are spatial frequencies in a Cartesian coordinate system. $T(u,v)$ is bandpass filtered by the human visual response $V(u,v)$, where $$V(u,v) = \exp\left[-\frac{(\ln\sqrt{u^2+v^2} - \ln(25u_o/D))^2}{2(0.973)^2}\right], \quad (1)$$

to obtain filtered data $(T(u,v)V(u,v))$, where $u_o$ and D are predetermined constants.

The RMS variation R, and the first moment of power spectrum, M are then determined, as follows:

$$R = \sqrt{\int_{\infty}^{\infty}\int_{\infty}^{\infty} V^2(u,v) T^2(u,v) \, du\, dv} \quad ; \text{and} \quad (2)$$

$$M = \frac{\int_{\infty}^{\infty}\int_{\infty}^{\infty} \sqrt{u^2+v^2}\, V^2(u,v) T^2(u,v)\, du\, dv}{\int_{\infty}^{\infty}\int_{\infty}^{\infty} V^2(u,v) T^2(u,v)\, du\, dv} \quad (3)$$

Once R and M are determined, as shown in FIG. 1, in step 30 the two texture measures R and M obtained from all ROIs of a PA chest image are normalized by using the average values and standard deviations derived from a data base for normal lungs. This data base has been obtained by the inventors by. determining the texture measures R and M for 100 normal lungs, as well as 100 abnormal lungs with nodular, reticular and honeycomb patterns. Then, in step 40 a single texture index is determined from the two normalized texture measures by taking into account the distribution, i.e., the data base, of texture measures obtained from abnormal lungs. Then, in step 50, ROIs with large texture indices above a predetermined threshold value are selected. These selected ROIs are finally subjected to three independent test in steps $60_1$, $60_2$ and $60_3$ for a definitely abnormal singular pattern (step $60_1$), a localized abnormal pattern (step $60_2$), or a diffuse abnormal pattern (step $60_3$) A chest image containing any one of the abnormal patterns is classified as indicating an abnormal lung with interstitial disease in step 70. Otherwise if none of the abnormal patterns are present, the lung is classified as normal in step 80.

The two texture measure are normalized in step 30 by means of the average and the standard deviation of texture measures obtained for normal lungs that are included in the data base, as shown by the two equations below:

$$R_N = \frac{R - R^-}{\sigma_R}, \quad (4)$$

$$M_N = \frac{M - M^-}{\sigma_M}, \quad (5)$$

where $R_N$ and $M_N$ are the normalized rms variation and the normalized first moment of the power spectrum, respectively; $R^-$ and $M^-$ are the average rms variation and the average first moment of the power spectrum for normal lungs, respectively; and $\sigma_R$ and $\sigma_M$ are the standard deviation of the rms variation and the standard deviation of the first moment of the power spectrum for normal lungs, respectively.

Figure 2:
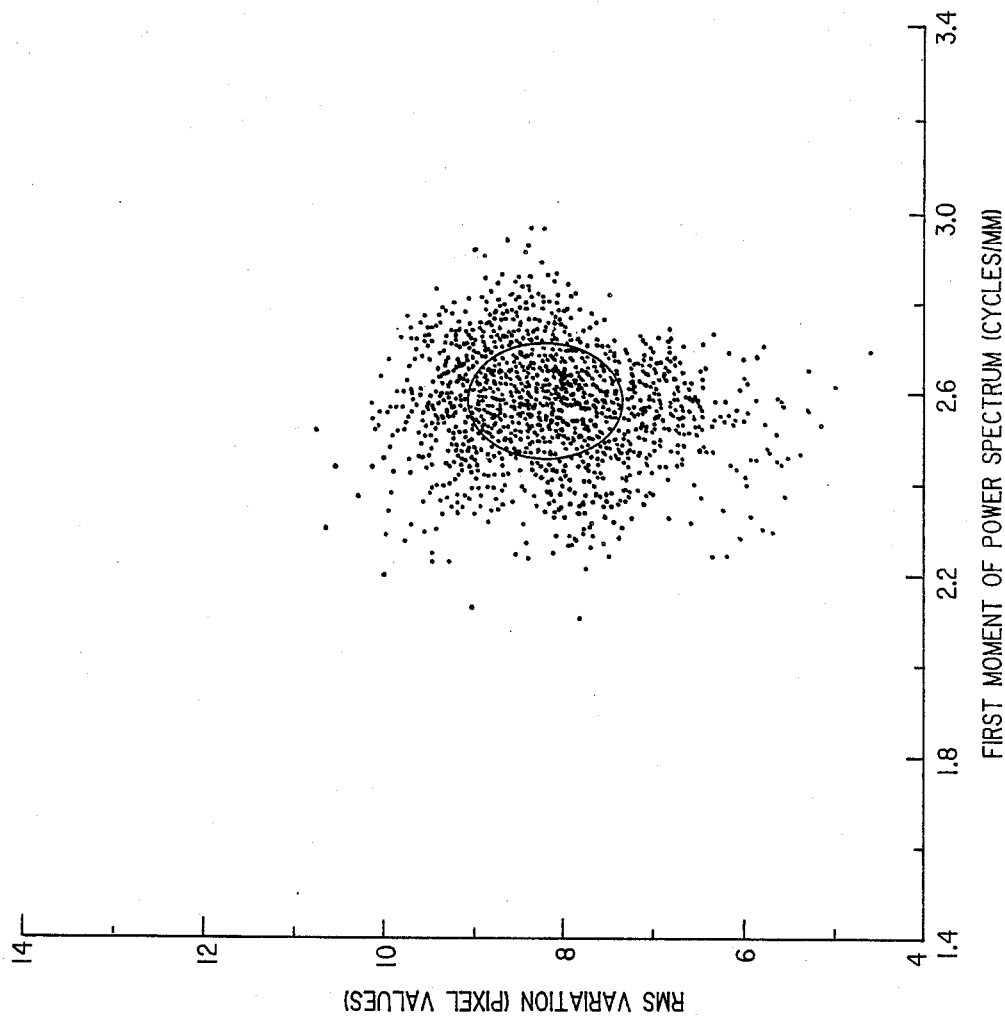
FIG. 2 is a graph illustrating the distribution of the two texture measures, RMS variation (R) and first moment of power spectrum (M), obtained for normal lungs and forming the data base for normal lungs by which classification according to the present invention is performed.

The distribution of the two texture measures obtained for normal lungs is shown in FIG. 2. From this distribution, it has been determined that the average and the standard deviation of the rms variation for normal lungs are 8.190 and 0.884 in terms of pixel value unit, respectively, and the average and the standard deviation of the first moment of the power spectrum are 2.577 cycles/mm and 0.120 cycles/mm, respectively. The pixel value unit used for the rms variation can be converted to other units, which may be useful in situations when the rms variation may be determined in terms of the optical density or relative x-ray intensity. Since radiographic images were digitized in this study with a high-quality drum scanner by using a 10 bit analog-to-digital conversion and by mapping linearly the optical density range from 0.4 to 2.2 to the pixel values in the range of 800 to 200 (i.e., 0.003 optical density/pixel value), the average and the standard deviation of the rms variation for normal lungs are 0.02457 and 0.002652 in terms of optical density unit, respectively.

The average and the standard deviation of the rms variation in terms of the relative x-ray intensity can be obtained by dividing these quantities in terms of optical density by a factor of 0.434G, where G is the gradient of the characteristic curve of a screen-film system used for chest radiographs. By assuming the average gradient of 2.8, it is estimated that the average and the standard deviation of the rms variation for normal lungs will be approximately 0.02 and 0.002 in terms of relative x-ray intensity, respectively. It should be noted that these quantities in terms of relative x-ray intensity provide only rough estimates and should be used cautiously, since the characteristic curves for all radiographic images are not known and only the average curve was employed to obtain the average gradient.

Figure 3:
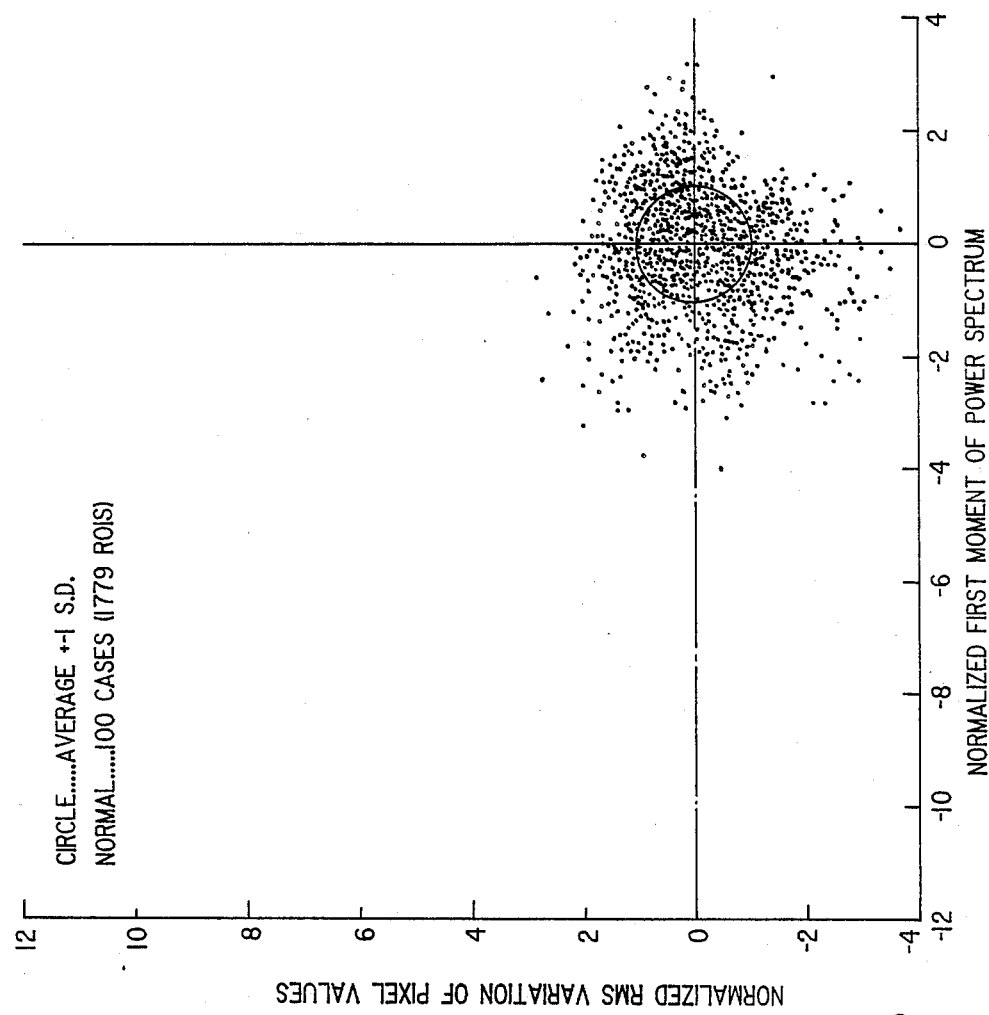
FIG. 3 is a graph illustrating the distribution of normalized texture measures obtained from 100 chest images of normal lungs, wherein the circle indicates ± one standard deviation.
Figure 4:
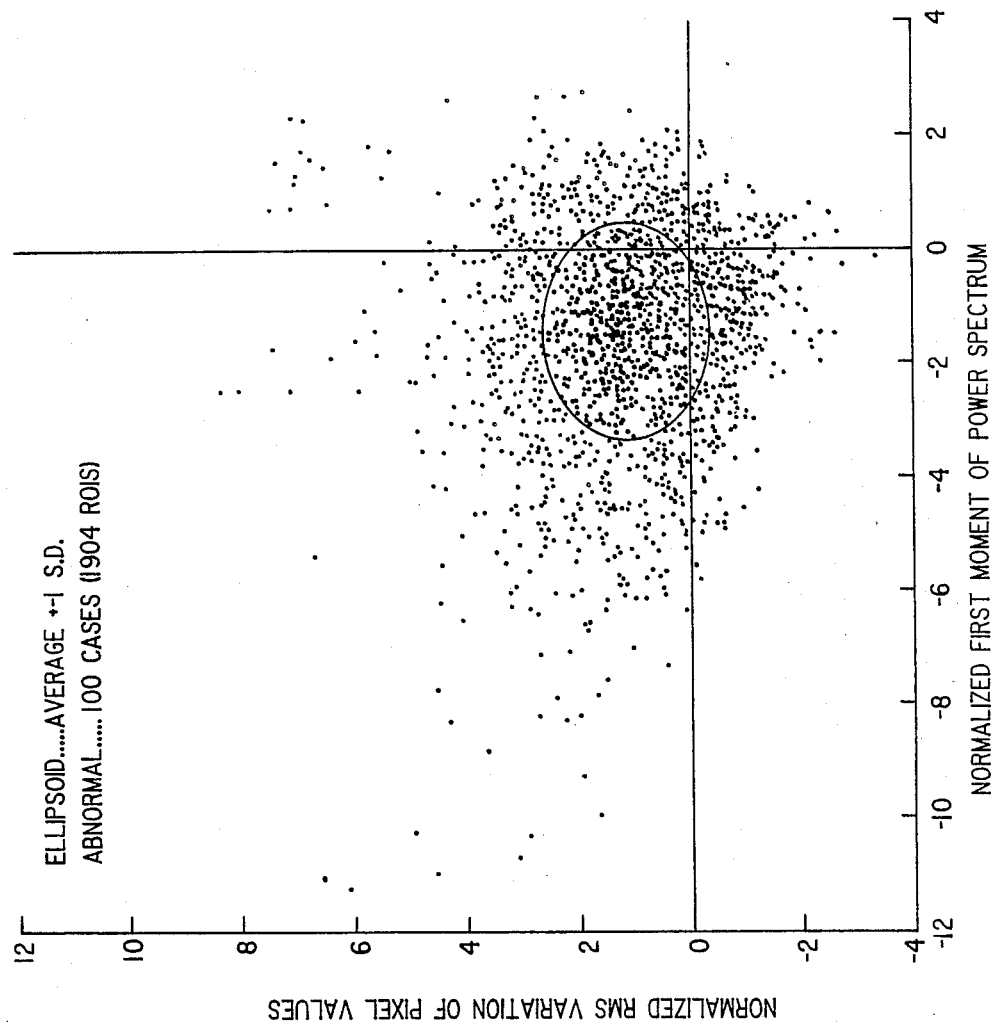
FIG. 4 is a graph illustrating the distribution of normalized texture measures obtained from 100 chest images of abnormal lungs, wherein the ellipsoid indicates the range of the average ± one standard deviation.

The distributions of the normalized texture measures for normal and abnormal lungs in the data base are shown in FIGS. 3 and 4, respectively. The distribution for normal lungs is centered around the origin of the normalized texture measure coordinates, whereas the distribution for abnormal lungs is shifted to the upper left. However, there is obviously a considerable overlap between the two distributions. This is because lung textures included in an abnormal lung can comprise some normal areas, unless the interstitial disease is spread over the entire lungs. Therefore, it is expected that a classification scheme based only on these distributions will not be very effective in distinguishing between normal and abnormal lungs.

Figure 5:
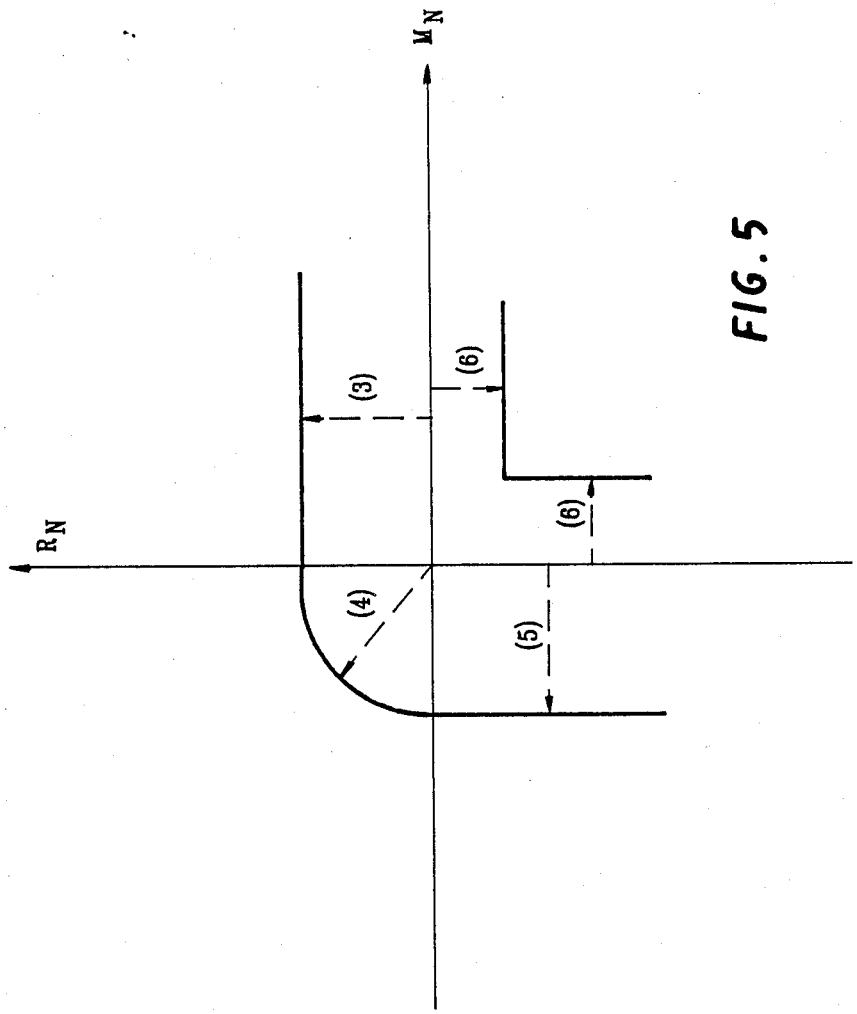
FIG. 5 is an illustration of a single texture index (T), determined from normalized texture measures, in order to facilitate computerized classification of normal and abnormal lungs, wherein the texture index (T) in the four quadrants is defined by predetermined equations and is illustrated by dotted arrows.

Because the distribution of texture measures for abnormal lungs includes some values for normal lungs and thus is shifted to the second quadrant of the normalized texture measure coordinates, step 40 is performed to formulate a new single texture index (T) as illustrated in FIG. 5, thereby to distinguish effectively between normal and abnormal lungs. The utility of a single figure of merit provided by a reliable index rather than by two parameters lies in the simplicity and efficiency of achieving an accurate automated classification by computer, as will become evident in the results which will be described hereinafter. Mathematically, the single texture index T is defined as follows:

In the first quadrant, i.e., $$M_N > 0 \text{ and } R_N > 0, T = R_N. \quad (6)$$

In the second quadrant, i.e., $$M_N < 0 \text{ and } R_N > 0, T = \sqrt{M_N^2 + R_N^2}. \quad (7)$$

In the third quadrant, i.e., $$M_N < 0 \text{ and } R_N < 0, T = -M_N. \quad (8)$$

In the fourth quadrant, i.e., $$M_N > 0 \text{ and } R_N < 0, T = -\{Min(M_N), |R_N|\}, \quad (9)$$

i.e., the negative of the smaller of $M_N$ or the absolute value of $R_N$.

Figure 6:
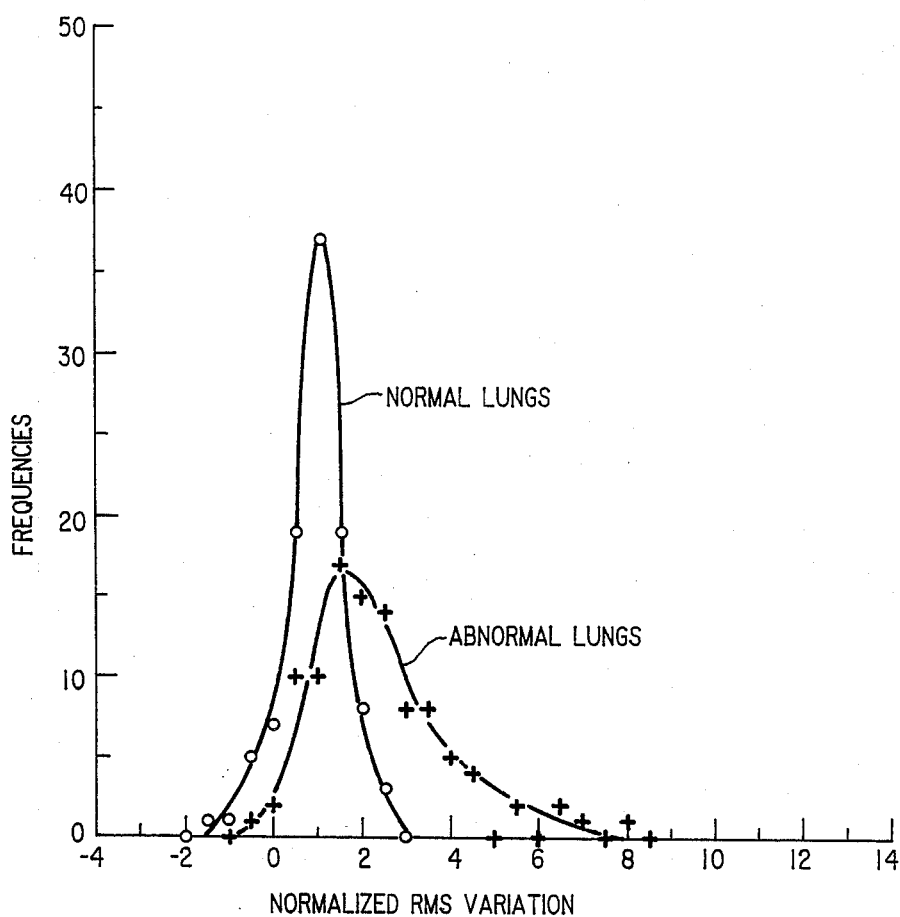
FIG. 6 are histograms of the maximum value of normalized rms variations included among all ROIs selected in each chest image for normal and abnormal lungs.
Figure 7:
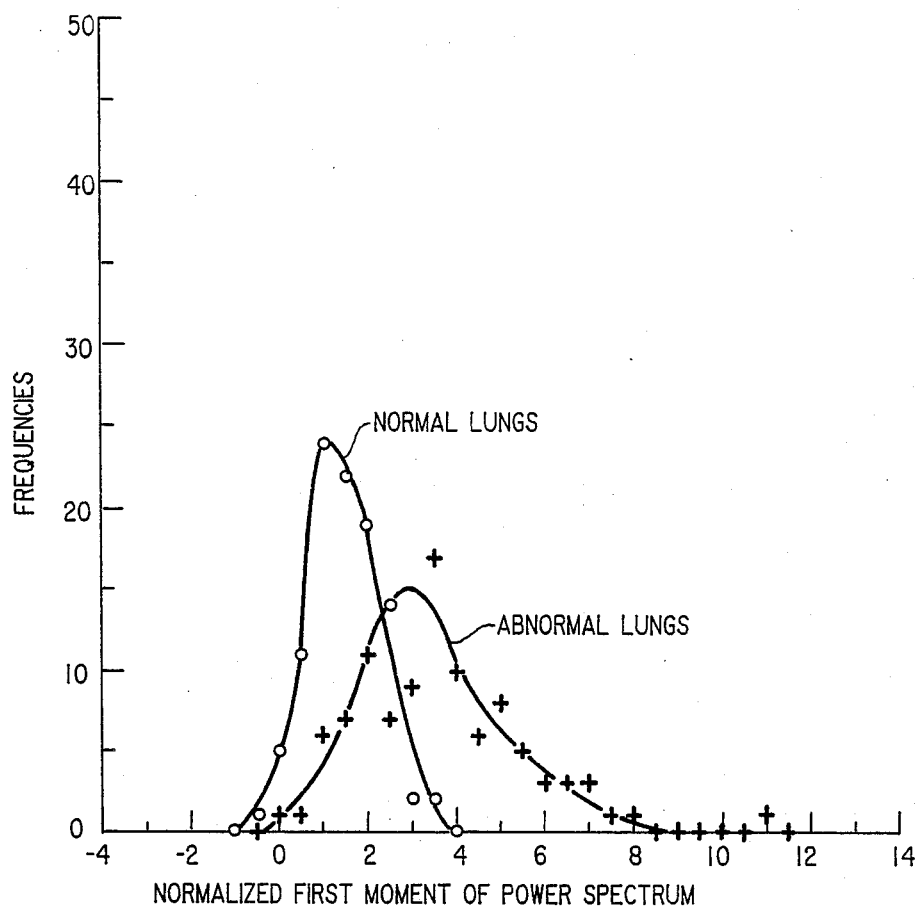
FIG. 7 are histograms of the maximum value of normalized first moments of power spectra included among all ROIs selected in each chest image for normal and abnormal lungs.
Figure 8:
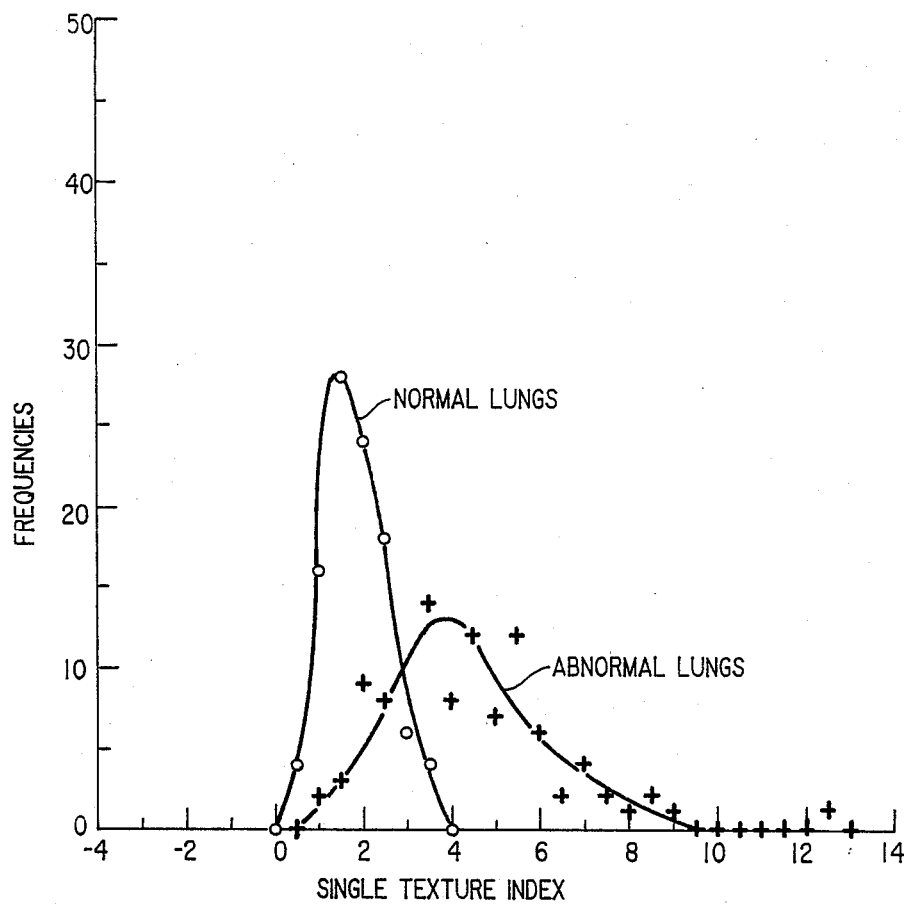
FIG. 8 are histograms of the maximum value of texture indices included among all ROIs selected in each chest image for normal and abnormal lungs.
Figure 9:
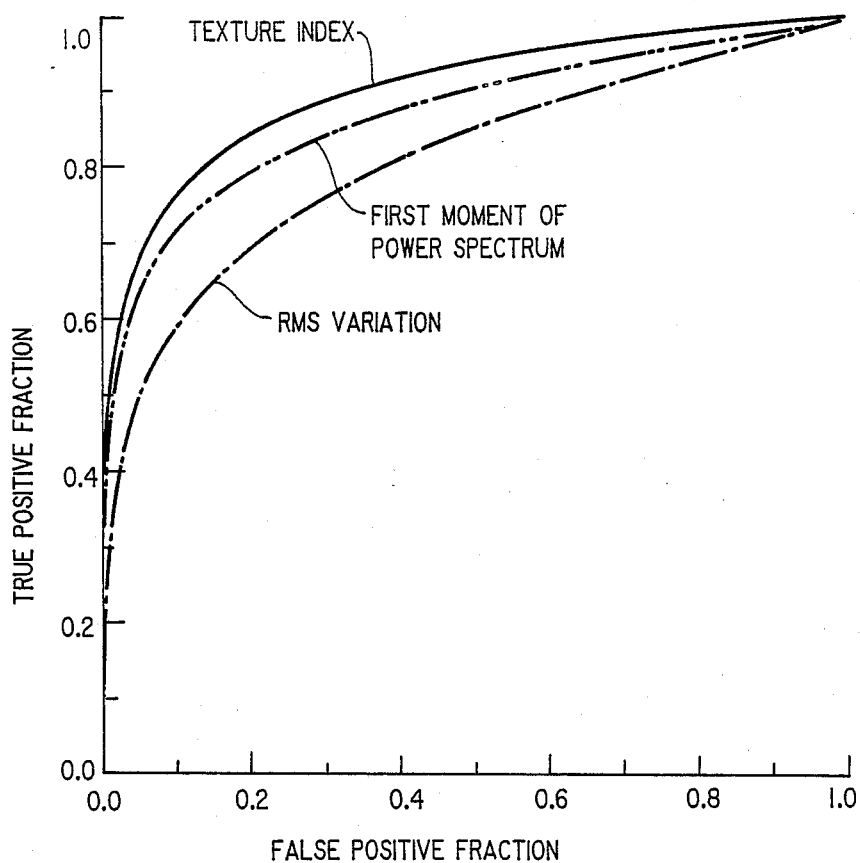
FIG. 9 is a graph illustrating receiver operating characteristic (ROC) curves for distinction between normal and abnormal lungs by computer as based on the RMS variation, the first moment of the power spectrum, or the single texture index, wherein it is seen that the texture index is more effective than is either of the two texture measures alone.

The usefulness of the texture index, T, is demonstrated by comparison of the histograms of the rms variations, the first moments of the power spectra, and the new texture indices for normal and abnormal lungs, as shown in FIGS. 6, 7, and 8, respectively. These histograms illustrate the frequencies of occurrence of the maximum value included among all the ROIs for each chest image. It is apparent that the histograms of the rms variation and of the first moment of the power spectrum for abnormal lungs overlap considerably with those for normal lungs. Therefore, it is difficult to distinguish between normal and abnormal lungs if the maximum value of either the rms variation or the first moment of the power spectrum is employed for their classification. However, the histograms of the single texture index show an improved separation between the distributions for normal and abnormal lungs, thus indicating improved performance in their classification. In fact, this result is confirmed when the receiver operating characteristic (ROC) curves are plotted as shown in FIG. 9. (For a description of ROC analysis techniques, see C. E. Metz, Investigative Radiology 21:720–733 (1986)). The ROC curve is known at present as the most reliable diagram which indicates the performance of detectors (or observers) in distinguishing between two possible states, such as normal and abnormal, for lungs. The ROC curve is generally a plot of the relationship between the true positive fraction, i.e., the fraction of correct classifications (or detections) of the abnormal lung as abnormal, and the false-positive fraction, i.e., the fraction of incorrect classifications (or detections) of the normal lung as abnormal. This relationship is expressed by a curve instead of a point because these fractions can change depending upon the threshold level used.

In particular, referring to FIGS. 8 and 9, for example, in producing the ROC curve labelled "texture index" in FIG. 9, a texture index threshold is established with respect to the histograms shown in FIG. 8. For each possible threshold value, the true positive fraction is determined as the ratio of the area under the curve of the abnormal lung histogram to the right of the threshold value to the total area under the curve of the abnormal lung histogram. Similarly, the false positive fraction is determined as the ratio of the area under the curve of the normal lung histogram to the right of the threshold value to the total area under the curve of the normal lung histogram. For example, as the threshold level decreases, the true-positive fraction is expected to increase, but the false-positive fraction also increases. In comparisons of different ROC curves obtained with different detectors or methods, the higher (or the closer to the top left corner) the ROC curve is, the better the performance in general. Therefore, FIG. 9 indicates clearly that the use of the texture index is superior to either the use of the rms variation or to that of the first moment of the power spectrum in the automated classification of lung textures for normal lungs and lungs that are abnormal due to interstitial disease.

In order to improve the performance of the automated classification method of the invention further, three independent tests $60_1$, $60_2$ and $60_3$ for abnormal patterns that are included in abnormal lungs with interstitial disease are performed. The first test $60_1$ is designed to examine whether any texture index obtained from all ROIs selected in a chest image has a value greater than four. If so, the chest image is classified as abnormal, because there are no normal lungs in the data bas which contain a texture index greater than four, as is illustrated in FIG. 8. When the method of the invention scheme is applied for daily use in the analysis of a large number of clinical cases, there may be some normal cases in which the texture index is larger than four, and these will contribute to an increase in the false-positive fraction. However, it is believed that this increase will be very small in view of the fact that none of the 100 normal chest images in the data base yielded a texture index larger than four.

The second test $60_2$ is intended to examine whether preselected "abnormal" ROIs with a texture index relatively high above the threshold level are clustered within a certain predetermined distance (or diameter of a circle). The threshold level for the texture index can be changed by use of an interactive selection control or by an automated method, or it can be set to a predetermined level. The effect of the distance in the range of 1 cm to 5 cm on the determination of clustered abnormal ROIs has been examined in the derivation of the present invention. A distance of approximately 3-4 cm was found to be effective in allowing detection of localized abnormal patterns due to interstitial disease, and the inclusion of this test clearly improved the performance, as shown by the ROC curves in FIG. 10.

Figure 10:
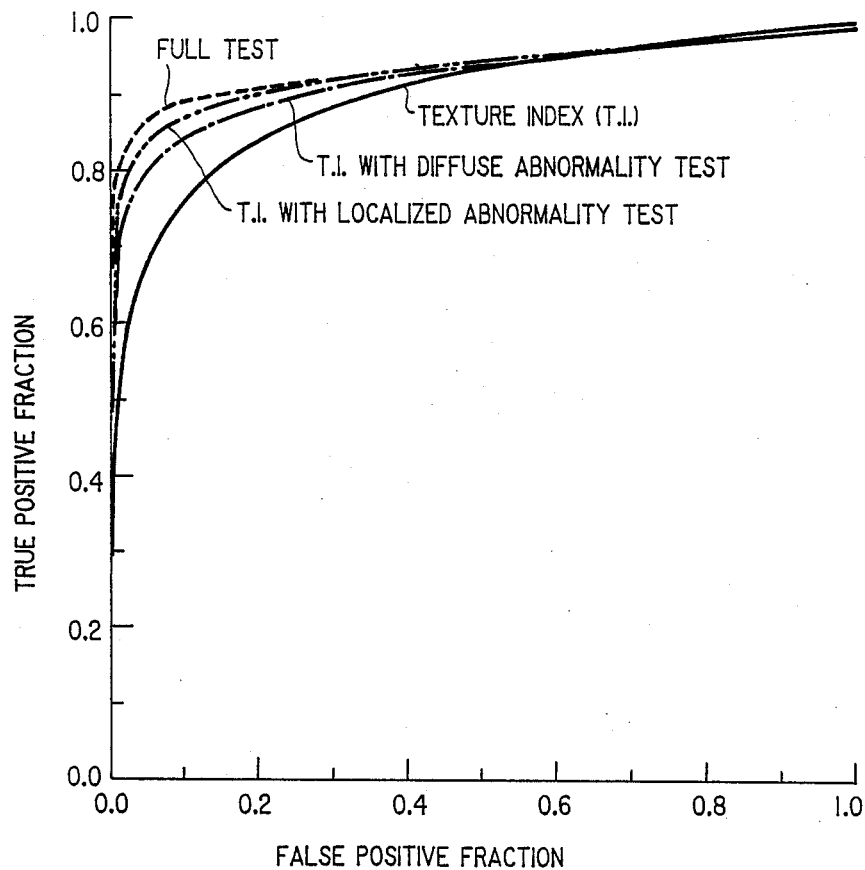
FIG. 10 is a graph illustrating ROC curves for distinction between normal and abnormal lungs by computer when the texture index is used together with the localized and/or diffuse abnormality test, from which it is seen that the full test scheme shown in FIG. 1 provides the best performance.

The third test $60_3$ examines whether preselected abnormal ROIs are spread over the entire lung and constitute a diffuse abnormal pattern due to interstitial disease. In test $60_3$, the total number of these ROIs per chest image which yield a texture index above the threshold level is counted. The results indicated that, when there were more than four abnormal ROIs, the chest image was very likely to include a diffuse abnormal pattern due to interstitial disease. The usefulness of test $60_3$, as well as the overall result of employing these three tests together, are illustrated in FIG. 10. From this result, and from other data which are included for comparison with the performance of radiologists as will be discussed later, it is confirmed that the full test as illustrated in FIG. 1 provided the best performance result. It should be noted that the optimal criteria used for both the distance (or diameter) of the localized abnormal area and the total number of abnormal ROIs for these tests can change if the total number of ROIs selected per chest image is increased significantly.

The methods and procedures described above in terms of the normalization, the single texture index, and the test for abnormality have been applied to the entire lung for each chest image. However, the same methods and procedures can be applied independently to selected lung areas in different locations such as the upper, middle, and lower lung as well as the inner lung and the outer lung. A data base for lung textures in both normal and abnormal lungs will then need to be established for each area selected. The normalization of texture measures is then achieved independently for each lung area by using the data base for normal lungs obtained from the corresponding lung area. The texture index is determined by the method described by equations 6-9 and illustrated in FIG. 5. Tests for abnormal lungs are performed independently in each lung area.

It has been found that this approach to the automated classification scheme as applied to partial lung areas is slightly more sensitive in distinguishing between normal and abnormal lungs than that applied to entire lung. However, since the data base is limited at present, it was not possible to confirm the statistical significance of this slight improvement in sensitivity. Apparently a larger data base for texture measures is required for implementation of this approach to partial lung areas.

In order to evaluate the usefulness of our computerized automated classification scheme, the method of the invention has been applied to the analysis of clinical cases which were used previously for studies of the effect of the display format on diagnostic accuracy in digital chest radiography. This study included a comparison of hard-copy, video, and reversed grey scale images (H. MacMahon, C. E. Metz, K. Doi, T. Kim, M. L. Giger, and H. P. Chan. Radiology 161(P):203, 1986 (abstract)). The sixty chest images selected for the study included subtle abnormalities such as pulmonary nodules, pneumothoraces, interstitial infiltrates, and bone lesions. ROC curves for detection of each of these abnormalities were obtained by six staff radiologists and six senior radiology residents.

Figure 11:
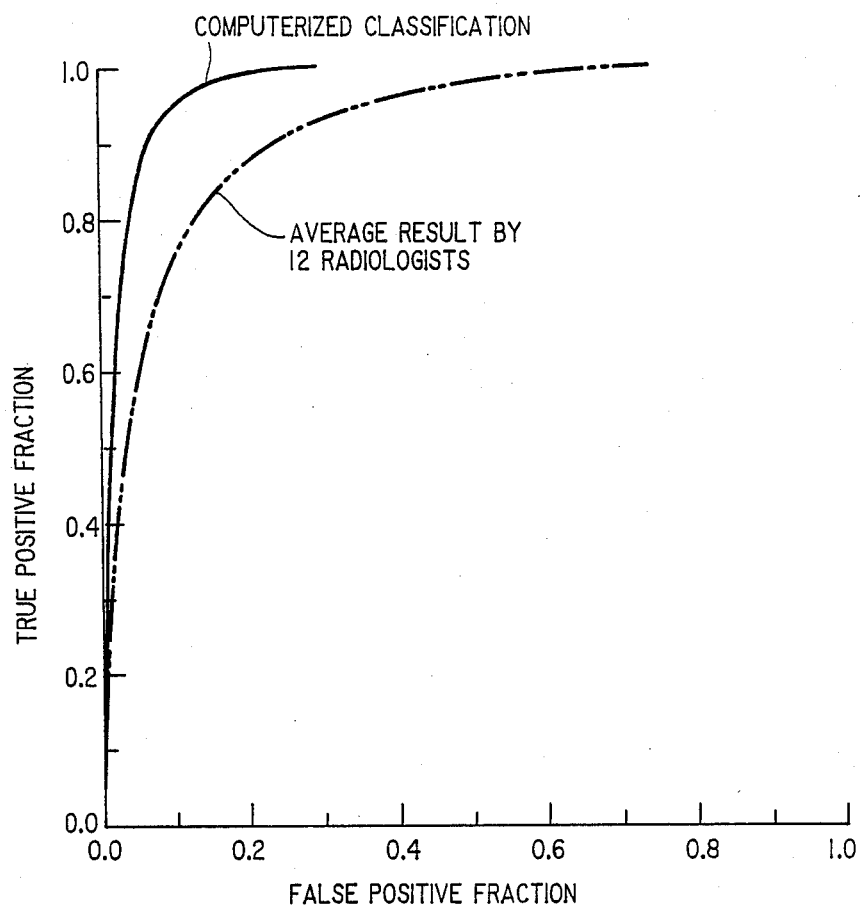
FIG. 11 is a graph illustrating a comparison of ROC curves obtained by computer and by 12 radiologists on 60 selected chest images (not included in the data base of FIG. 2), from which it is seen that the present invention was superior to the performance of radiologists in distinguishing between normal lungs and abnormal lungs with interstitial infiltrates.

FIG. 11 shows a comparison of the ROC curves obtained by these twelve observers and by the automated classification method of the present invention. It is apparent that the computerized approach yields results superior to those obtained by the average observers in distinguishing between normal and abnormal lungs with interstitial infiltrates. It should be noted that the chest images used for observer performance studies were prepared with a 0.3 mm pixel size and a drum scanner which provided high-quality hard-copy images, whereas the automated classification was applied to digital image data obtained with a 0.1 mm pixel size. It is expected that the ROC curve obtainable by radiologists may be improved if hard-copy images with 0.1 mm pixel size are provided for observer performance studies. However, this improvement would not be very great, as has been indicated previously in observer performance studies regarding the effect of pixel size on the detection of interstitial infiltrates (H. M. MacMahon, C. J. Vyborny, C. E. Metz, K. Doi, V. Sabeti, and S. L. Solomon, Radiology 158:21, (1986)). Therefore, it is believed that the conclusion derived from the results in FIG. 11 remains, namely, the computerized approach according to the present invention can provide better performance than can human observers in detecting abnormal lungs with interstitial diseases.

From the analysis of texture measures obtained for abnormal lungs in the data base above-discussed, it has been found that abnormal lungs with a reticular pattern tend to contain large rms variations, and a relatively high first moment of the power spectrum which is comparable to that for normal lungs. The result corresponds to the finding that normalized texture measures of a reticular pattern are generally distributed near the upper part of the positive $R_N$ axis. For abnormal lungs with a nodular pattern, the first moment of the power spectrum tends to be lower than that for normal lungs, but the rms variation is comparable to that for normal lungs. This result corresponds to a distribution of normalized texture measures of a nodular pattern that is generally located near the left part of the negative $M_N$ axis. However, abnormal lungs with honeycomb and reticulo-nodular patterns tend to contain an rms variation larger than that for normal lungs and a first moment of the power spectrum lower than that for normal lungs. This implies that the normalized texture measures of honeycomb and reticulo-nodular patterns are located in the second quadrant of the ($M_N$, $R_N$) coordinates, near the upper left of the diagonal axis drawn from the origin.

Based on the findings on these image features of various abnormal patterns due to interstitial disease obtained according to the present invention, abnormal lung areas are represented by special markers (or symbols) which are superimposed on a chest image displayed for the radiologist's interpretation. Typically, a high-resolution CRT monitor is employed for display; however, other types of display devices, including film images, can be used for this purpose. When a chest image is classified as abnormal based on the automated scheme shown in FIG. 1, all of the abnormal ROIs containing a texture index above the threshold level are displayed with three types of symbols which are superimposed on the chest image at the location of the abnormal ROIs and which represent the nature and magnitude of each abnormality in each ROI.

Figure 12:
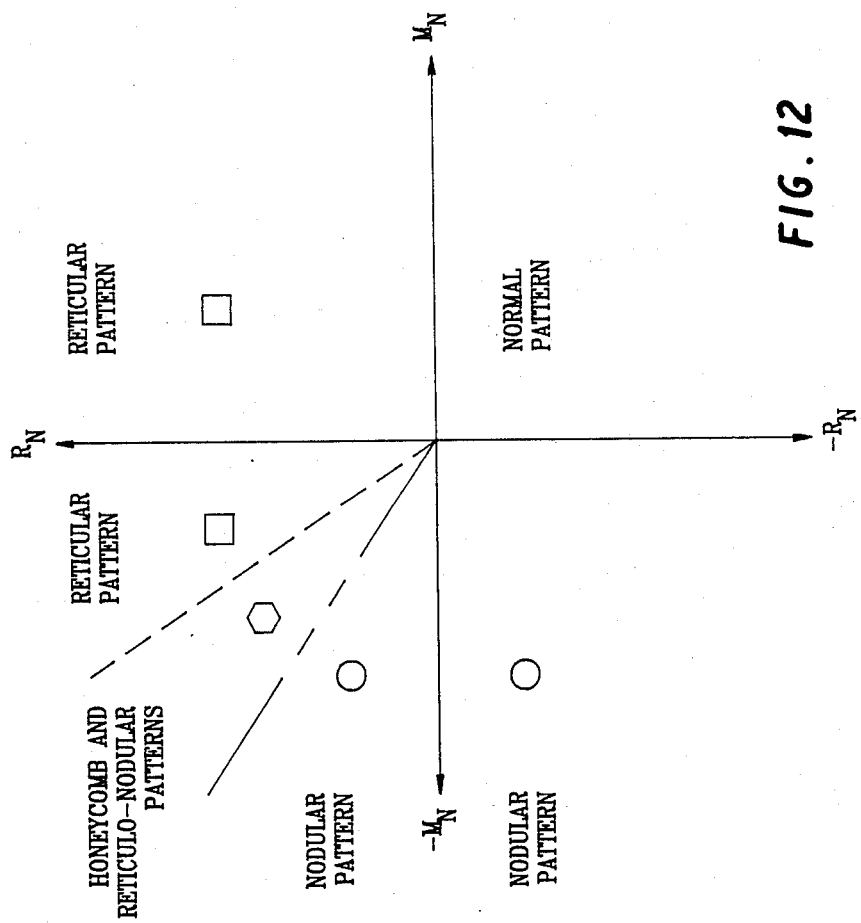
FIG. 12 is an illustration of three different regions in the texture measure coordinate system, and symbols used to represent reticular, nodular, and honeycomb (and reticulo-nodular) patterns by square, circle, and hexagon, respectively.

As illustrated in FIG. 12, the squares represent reticular patterns when abnormal texture measures are located in the first quadrant or in the one-third of the second quadrant which is adjacent to the first quadrant (as indicated by the ordinate and the dotted line that lies at 30 degrees from the ordinate). The circles represent nodular patterns when abnormal texture measures are located in the third quadrant or in the one-third of the second quadrant which is adjacent to the third quadrant (as indicated by the abscissa and the dot-dash line that lies at 30 degrees from the abscissa). Hexagons represent honeycomb and reticulo-nodular patterns when abnormal texture measures are located in the one-third portion of the second quadrant which is the area between the dotted line and the dot-dash line. The magnitude of the abnormality is indicated by the size of these symbols; the greater the texture index of an abnormal ROI, the larger the size of the circle, hexagon, or square. The center of the symbol is located at the center of the ROI selected in the chest image. The size of a symbol can be changed in proportion to the texture index, or by other relationships which provide a monotonic increase in size as the texture index increases. The sizes or areas of the three different symbols are kept the same when the magnitudes of the corresponding texture indices are the same.

Other quantities displayed on the CRT monitor which are very useful are the true-positive fraction and the false-positive fraction, which are derived from the ROC curve at the operating point, namely, at the threshold texture index used. This has important implications in terms of the judgment criteria concerning the reliability of the computer output when it indicates an abnormal lung, since the true-positive fraction and the false-positive fraction represent the probability of an abnormal lung and the possibility of a normal lung, respectively, when a chest image is classified as abnormal by the automated classification method of the present invention. In other words, the present method can show the probability that the lung is indeed abnormal and also the probability that the lung can actually be normal even if the computer output indicates an abnormal lung.

Since an ROC curve such as that shown in FIG. 10 is derived by variation of the threshold level of the texture index, the data for this curve, together with the corresponding threshold level, can be stored in the computer. Therefore, when a chest image is analyzed at a predetermined threshold level, the corresponding values for the true-positive fraction and the false-positive fraction at this threshold level can be displayed on the monitor when the chest image is classified as abnormal due to interstitial disease. In addition, when the chest image is analyzed interactively by varying the threshold level, the corresponding variations in these fractions at different threshold levels, as well as abnormal ROIs above the threshold level, can be displayed immediately as this level is changed. These displays of the nature, magnitude, and probability concerning abnormal lung textures will greatly facilitate the radiologist's diagnosis of interstitial disease as seen on chest radiographs.

When a chest image is classified as normal with the present automated classification scheme, two important parameters are displayed on the CRT monitor in a way similar to that in the case of an abnormal lung. These parameters are the probability that the lung is indeed normal, i.e., the true-negative fraction, which equals one, minus the false-positive fraction, and the probability that the lung is actually abnormal, i.e., the false-negative fraction, which equals one, minus the true-positive fraction. It is apparent that these probabilities can be determined from the ROC curve, and that they will be useful as judgment criteria concerning the reliability of a normal lung as indicated by the computer.

Figure 13:
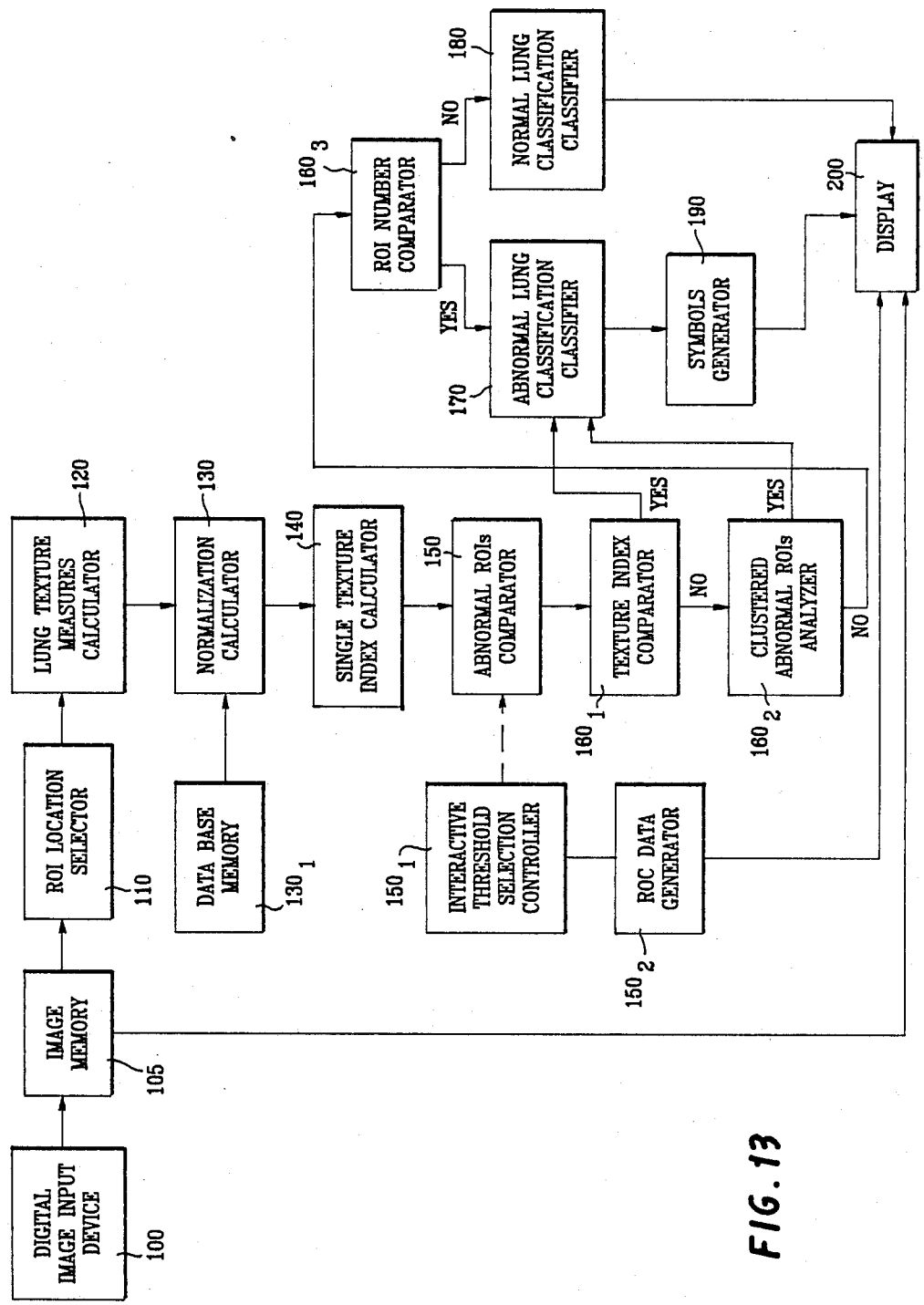
FIG. 13 is a schematic block diagram illustrating the method and the system of automated classification for lung texture analysis on digital chest images, according to the present invention.

FIG. 13 is a schematic block diagram illustrating in sequential form the operation of a hard-wired automated classification system for the analysis of lung textures in digital chest images. First, digital image data corresponding to a given chest radiograph are input by means of input device 100 and stored in an image memory 105. A digital chest image can be obtained by digitization of a conventional radiographic film image, or by other digital devices such as the Picker line-scanned digital chest system, AS&E point-scanned digital system, Fuji storage phosphor and laser-readout digital system, image intensifier-TV digital system, or selenium plate digital system. Appropriate ROIs are then selected manually or automatically, (block 110), and texture measures R and M on the selected ROIs are determined (block 120). Texture measures R, M are normalized in normalization calculator 130 based on the data base statistics for normal lungs stored in the data base memory $130_1$. Normalized texture measures are then applied to the calculator 140 which calculates a single texture index T(M,R), as above discussed in relation to FIG. 5. The single texture index T(M,R) from the calculator 140 is then applied to comparator 150, which compares the texture index for each ROI against a threshold value which can be interactively selected by means of interactive threshold selection controller $150_1$. Controller $150_1$ also applies a selectable threshold to ROC generator $150_2$, which stores ROC data and based on a selected threshold value applied by controller $150_1$ produces false-positive data and true-positive data, at the selected threshold index. Also provided are comparator $160_1$ which determines if the texture index of each ROI exceeding the threshold set by controller $150_1$ as determined by comparator 150 is greater than 4; the analyzer $160_2$ which determines whether the ROIs, which are not judged to be abnormal by comparator $160_1$, are clustered within a predetermined distance (or diameter of a circle); and the comparator 160₃ which determines whether the total number of ROIs exceeding the threshold set by controller 150₁ as determined by comparator 150 is greater than four. If any of comparators 160₁, 160₃ and analyzer 160₂ yield a positive determination then an abnormal lung classification is made by classifier 170. If not, a normal lung classification is made by normal lung classifier 180.

Also provided is symbols generator 190 which generates symbols indicative of the type of abnormality (e.g., honeycomb, reticular, reticulo-nodular, nodular etc. as above discussed) with each symbol having a size indicative of the degree of abnormality, i.e., in proportion to the texture index.

According to the invention, a display 200, such as a CRT monitor, is provided to display the image, the symbols generated by generator 190 at the location of abnormal ROI, as well as ROC information from generator 150₂, as above discussed.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for automated classification of distinction between normal and abnormal lungs with interstitial disease in digital chest radiographs, comprising:
  sampling plural regions of interest (ROIs) of a subject digital radiograph;
  producing digital data indicative of the texture of each of said ROIs;
  determining from the digital data of each selected ROI texture measures indicative of the lung texture of the respective ROIs;
  normalizing the texture measures determined in said determining step in relation to predetermined characteristics derived from a data base of normal lungs; and
  processing normalized texture measures obtained in said normalizing step to determine based on predetermined criteria whether or not a lung image of the subject digital radiograph is normal or abnormal.

2. The method according to claim 1, wherein said determining step comprises:
  removing non-uniform background trend in the digital data of each ROI in order to isolate underlying fine texture;
  determining the power spectrum of the underlying fine texture;
  bandpass filtering the determined power spectrum;
  determining the root-mean-square (RMS) variation (R) and the first moment of the power spectrum (M) of the bandpass filtered power spectrum; and
  using R and M as said predetermined texture measures.

3. The method according to claim 2, wherein said normalizing step comprises:
  determining normalized values of $R_N$ and $M_N$ based on the following relationships, $$R_N = \frac{R - R^-}{\sigma_R};$$

-continued
$$M_N = \frac{M - M^-}{\sigma_M};$$

where $R^-$ and $M^-$ are respectively the average RMS variation and the average first moment of the power spectrum for normal lungs as derived from said data base, and $\sigma_R$ and $\sigma_M$ are respectively the standard deviations of the RMS variation and the first moment of the power spectrum for normal lungs, respectively.

4. The method according to claim 3, wherein said processing step comprises:
  calculating a single texture index (T) based on the normalized values of $R_N$ and $M_N$.

5. The method according to claim 4, wherein T is defined in $(M_N, R_N)$ coordinates as follows:
  $T = R_N$, for a first quadrant where $M_N > 0$ and $R_N > 0$,
  $T = \sqrt{M_N^2 + R_N^2}$, for a second quadrant where $M_N < 0$ and $R_N > 0$,
  $T = -M_N$, for a third quadrant where $M_N < 0$ and $R_N < 0$, and
  $T = -\{\text{Min}(M_N, |R_N|)\}$ for a fourth quadrant where $M_N > 0$ and $R_N < 0$.

6. The method according to claim 4, wherein said processing step comprises:
  comparing the texture index T of each selected ROI against a first threshold value; and
  determining whether or not each ROI is potentially abnormal if the respective texture index exceeds said first threshold value in said comparing step.

7. The method according to claim 6, wherein said processing step comprises:
  comparing the texture index T of those ROIs determined to be potentially abnormal against a second threshold value; and
  determining the existence of an abnormal ROI pattern if any texture index T exceeds said second threshold value.

8. The method according to claim 7, wherein said processing step comprising:
  determining whether those ROIs determined to be potentially abnormal are clustered within a predetermined distance of each other; and
  determining the existence of an abnormal ROI pattern if it is determined that the potentially abnormal ROIs are clustered within said predetermined distance of each other.

9. The method according to claim 8, wherein said processing step comprises:
  counting the number of said potentially abnormal ROIs; and
  determining the existence of an abnormal ROI pattern if the number of potentially abnormal ROIs exceeds a third predetermined threshold value.

10. The method according to claim 9, wherein said processing step comprises:
  determining whether any abnormal ROIs are reticular, nodular, or honeycomb and reticulo-nodular based on the respective quadrant of $(M_N, R_N)$ coordinates and the location within a quadrant of said $(M_N, R_N)$ coordinates of the ROIs.

11. The method according to claim 10, comprising:
  displaying the image formed on said digital radiograph; and
  identifying on the displayed image those ROIs corresponding to any abnormal ROI pattern.

12. The method according to claim 11, comprising:

displaying respective abnormality symbols identifying particular abnormal ROIs of abnormal ROI patterns as being reticular, nodular, or honeycomb and reticulo-nodular on the displayed image at the location of the respective abnormal ROI in the displayed image.

13. The method according to claim 12, comprising:
varying the size of each abnormality symbol in relation to the magnitude of the texture index T of the respective ROI.

14. The method according to claim 13, comprising:
deriving a receiver operating characteristic (ROC) curve as a function of said first threshold value in terms of the variation of a true positive fraction versus a false-positive fraction of ROIs determined to be abnormal; and
displaying a true-positive fraction and a false-positive fraction in addition to said image and said abnormality symbols.

15. The method according to claim 14, further comprising:
interactively varying said first threshold value and displaying said image, said abnormality symbols and said true-positive and false-positive fractions as determined for a varied first threshold value.

16. The method according to claim 15, further comprising:
interactively varying said first threshold value and displaying said image, said abnormality symbols and said true-positive and false-positive fractions as determined for a varied first threshold value.

17. The method according to claim 13, comprising:
varying the size of each abnormality symbol in relation to the magnitude of the texture index T of the respective ROI.

18. The method according to claim 17, comprising:
deriving a receiver operating characteristic (ROC) curve as a function of said first threshold value in terms of the variation of a true positive fraction versus a false-positive fraction of ROIs determined to be abnormal; and
displaying a true-positive fraction and a false-positive fraction in addition to said image and said abnormality symbols.

19. The method according to claim 8, wherein said processing step comprises:
determining whether any abnormal ROIs are reticular, nodular, or honeycomb and reticulo-nodular based on the respective quadrant of ($M_N$, $R_N$) coordinates and the location within a quadrant of said ($M_N$, $R_N$) coordinates of the ROIs.

20. The method according to claim 19, comprising:
displaying the image formed on said digital radiograph; and
identifying on the displayed image those ROIs corresponding to any abnormal ROI pattern.

21. The method according to claim 20, comprising:
displaying respective abnormality symbols identifying particular abnormal ROIs of abnormal ROI patterns as being reticular, nodular, or honeycomb and reticulo-nodular on the displayed image at the location of the respective abnormal ROI in the displayed image.

22. The method according to claim 7, wherein said processing step comprises:
determining whether any abnormal ROIs are reticular, nodular, or honeycomb and reticulo-nodular based on the respective quadrant of ($M_N$, $R_N$) coordinates and the location within a quadrant of said ($M_N$, $R_N$) coordinates of the ROIs.

23. The method according to claim 6, wherein said processing step comprising:
determining whether those ROIs determined to be potentially abnormal are clustered within a predetermined distance of each other; and
determining the existence of an abnormal ROI pattern if it is determined that the potentially abnormal ROIs are clustered within said predetermined distance of each other.

24. The method according to claim 6, wherein said processing step comprises:
counting the number of said abnormal ROIs; and
determining the existence of an abnormal ROI pattern if the number of potentially abnormal ROIs exceeds a third predetermined threshold value.

25. A system for automated classification of distinction between normal and abnormal lungs with interstitial disease in digital chest radiographs, comprising:
means for sampling plural regions of interest (ROIs) of a subject digital radiograph for evaluation;
means for producing digital data indicative of the texture of each of said ROIs;
means for determining from the digital data of each selected ROI texture measures indicative of the lung texture of the respective ROIs;
means for normalizing the texture measures determined by said determining step in relation to predetermined characteristics derived from a data base of normal lungs; and
means for processing normalized texture measures obtained by said normalizing means to determine based on predetermined criteria whether or not a lung image of the subject digital radiograph is normal or abnormal.

26. The system according to claim 25, wherein said determining means comprises:
means for removing non-uniform background trend in the digital data of each ROI in order to isolate underlying fine texture;
means for determining the power spectrum of the underlying fine texture;
means for bandpass filtering the determined power spectrum;
means for determining the root-mean-square (RMS) variation (R) and the first moment of the power spectrum (M) of the bandpass filtered power spectrum;
wherein R and M are used as said predetermined texture measures.

27. The system according to claim 26, wherein said normalizing means comprises:
means for determining normalized values of $R_N$ and $M_N$ based on the following relationships, $$R_N = \frac{R - R^-}{\sigma_R};$$

$$M_N = \frac{M - M^-}{\sigma_M};$$

where $R^-$ and $M^-$ are respectively the average RMS variation and the average first moment of the power spectrum for normal lungs as derived from said data base, and $\sigma_R$ and $\sigma_M$ are respectively the standard deviations of the RMS variation and the first moment of the power spectrum for normal lungs, respectively.

28. The system according to claim 27, wherein said processing means comprises:
means for calculating a single texture index (T) based on the normalized values of $R_N$ and $M_N$;
wherein R is defined in $(M_N, R_N)$ coordinates as follows:
$T = R_N$, for a first quadrant where $M_N > 0$ and $R_N > 0$,
$T = \sqrt{M_N^2 + R_N^2}$ for a second quadrant where $M_N < 0$ and $R_N > 0$,
$T = -M_N$, for a third quadrant where $M_N < 0$ and $R_N < 0$, and
$T = -\{Min(M_N, |R_N|)\}$ for a fourth quadrant where $M_N > 0$ and $R_N < 0$.

29. The system according to claim 28, wherein said processing means comprises:
means for comparing the texture index T of each selected ROI against a first threshold value;
wherein it is determined whether or not each ROI is potentially abnormal if the respective texture index exceeds said first threshold value.

30. The system according to claim 29, wherein said processing means comprises:
means for comparing the texture index T of those ROIs determined to be potentially abnormal against a second threshold value; and
wherein the existence of an abnormal ROI pattern is determined if any texture index T exceeds said second threshold value.

31. The system according to claim 30, wherein said processing means comprises:
means for determining whether those ROIs determined to be potentially abnormal are clustered within a predetermined distance of each other;
wherein the existence of an abnormal ROI pattern is determined if it is determined that the potentially abnormal ROIs are clustered within said predetermined distance of each other.

32. The system according to claim 31, wherein said processing means comprises:
means for counting the number of said abnormal ROIs; and
means for determining the existence of an abnormal ROI pattern if the number of potentially abnormal ROIs exceeds a third predetermined threshold value.

33. The system according to claim 32, wherein said processing means comprises:
means for determining whether an ROI of any abnormal pattern of ROIs is reticular, nodular, or honeycomb and reticulo-nodular based on the respective quadrant of $(M_N, R_N)$ coordinates and the location within a quadrant of said $(M_N, R_N)$ coordinates of the ROI.

34. The system according to claim 33, comprising:
means for displaying the image formed on said digital radiograph; and
means for identifying on the displayed image those ROIs corresponding to any abnormal ROI pattern.

35. The system according to claim 34, comprising:
means for generating respective abnormality symbols identifying particular abnormal ROIs of abnormal ROI patterns as being reticular, nodular, or honeycomb and reticulo-nodular;
wherein said abnormality symbols are displayed on the displayed image at the location of the respective abnormal ROI in the displayed image.

36. The system according to claim 33, comprising:
means for varying the size of each abnormality symbol in relation to the magnitude of the texture index T of the respective ROI.

37. The system according to claim 36, comprising:
means for storing a receiver operating characteristic (ROC) curve as a function of said first threshold value in terms of the variation of a true positive fraction versus a false-positive fraction of ROIs determined to be abnormal; and
means for displaying a true-positive fraction and a false-positive fraction in addition to said image and said abnormality symbols.

38. The system according to claim 37, further comprising:
means for interactively varying said first threshold value so that said abnormality symbols and said true-positive and false-positive fractions vary a function of the varied first threshold value and are displayed in relation to a varied first threshold value.

39. The system according to claim 29, wherein said processing means comprising:
means for determining whether those ROIs determined to be potentially abnormal are clustered within a predetermined distance of each other;
wherein the existence of an abnormal ROI pattern is determined if it is determined that the potentially abnormal ROIs are clustered within said predetermined distance of each other.

40. The system according to claim 29, wherein said processing means comprises:
means for counting the number of said abnormal ROIs; and
means for determining the existence of an abnormal ROI pattern if the number of potentially abnormal ROIs exceeds a third predetermined threshold value.

41. The system according to claims 30, 39 or 40, wherein said processing means comprises:
means for determining whether an ROI of any abnormal pattern of ROIs is reticular, nodular, or honeycomb and reticulo-nodular based on the respective quadrant of $(M_N, R_N)$ coordinates and the location within a quadrant of said (MN, RN) coordinates of the ROI.

42. The system according to claim 41, comprising:
means for displaying the image formed on said digital radiograph; and
means for identifying on the displayed image those ROIs corresponding to any abnormal ROI pattern.

43. The system according to claim 42, comprising:
means for generating respective abnormality symbols identifying particular abnormal ROIs of abnormal ROI patterns as being reticular, nodular, or honeycomb and reticulo-nodular;
wherein said abnormality symbols are displayed on the displayed image at the location of the respective abnormal ROI in the displayed image.

44. The system according to claim 43, comprising:
means for varying the size of each abnormality symbol in relation to the magnitude of the texture index T of the respective ROI.

45. The system according to claim 44, comprising:
means for storing a receiver operating characteristic (ROC) curve as a function of said first threshold value in terms of the variation of a true positive fraction versus a false-positive fraction of ROIs determined to be abnormal; and means for displaying a true-positive fraction and a false-positive fraction in addition to said image and said abnormality symbols.

46. The system according to claim 45, further comprising:

means for interactively varying said first threshold value so that said abnormality symbols and said true-positive and false-positive fractions vary as a function of the varied first threshold value and are displayed in relation to a varied first threshold value.

* * * * *

UNITED STATES PATENT AND TRADEMARK OFFICE
CERTIFICATE OF CORRECTION

PATENT NO. : 4,839,807

DATED : June 13, 1989

INVENTOR(S) : KUNIO DOI, ET AL

It is certified that error appears in the above-identified patent and that said Letters Patent is hereby corrected as shown below:

In Column 1, line 20, before "BACKGROUND OF THE INVENTION" insert the following paragraph:

The present invention was made in part with U.S. Government support under grant number 2 R01 CA24806-11 from the Department of Health and Human Services and National Cancer Institute. The U.S. Government has certain rights in the invention.

Signed and Sealed this

Third Day of September, 1991

Attest:

HARRY F. MANBECK, JR.

Attesting Officer

Commissioner of Patents and Trademarks